United States Patent [19]

Hunt

[11] Patent Number: 4,856,344

[45] Date of Patent: Aug. 15, 1989

[54] MEASURING FLOW IN A PIPE

[75] Inventor: Andrew Hunt, Orwell, England

[73] Assignee: Schlumberger Technology Corporation, Houston, Tex.

[21] Appl. No.: 17,469

[22] Filed: Feb. 20, 1987

[30] Foreign Application Priority Data

Feb. 21, 1986 [GB] United Kingdom ............... 8604397

[51] Int. Cl.⁴ .............................................. G01F 1/74
[52] U.S. Cl. .............................. 73/861.04; 73/861.63; 73/61.1 R
[58] Field of Search ........... 73/861.02, 861.04, 861.63, 73/155, 861.03, 61.1 R

[56] References Cited

U.S. PATENT DOCUMENTS

| | | | |
|---|---|---|---|
| 2,023,568 | 12/1935 | Albersheim et al. | 73/861.63 |
| 2,767,580 | 10/1956 | Bevins et al. | 73/861.02 |
| 3,060,737 | 10/1962 | Arragon | 73/861.02 |
| 3,455,157 | 7/1969 | Lahaye et al. | 73/438 |
| 3,909,603 | 9/1975 | Nicolas | 364/300 |
| 4,127,332 | 11/1978 | Thiruvengadam | 366/131 |
| 4,231,262 | 11/1980 | Boll et al. | 73/861.04 |
| 4,312,234 | 1/1982 | Rhodes et al. | 73/861.04 |
| 4,430,251 | 2/1984 | Patterson et al. | 252/359 R |
| 4,441,361 | 4/1984 | Carlson et al. | 73/861.04 |
| 4,528,847 | 7/1985 | Halmi | 73/195 |
| 4,576,043 | 3/1986 | Nguyen | 73/195 |
| 4,604,902 | 8/1986 | Sabin et al. | 73/861.04 |
| 4,641,535 | 2/1987 | Malguarnera | 73/861.01 |
| 4,651,572 | 3/1987 | Albertz et al. | 73/861.63 |

FOREIGN PATENT DOCUMENTS

| | | |
|---|---|---|
| 142503 | 7/1980 | Fed. Rep. of Germany . |
| 1089203 | 11/1967 | United Kingdom . |
| 1552476 | 9/1979 | United Kingdom . |
| 1601699 | 11/1981 | United Kingdom . |
| 2085597 | 4/1982 | United Kingdom . |
| 2124781 | 2/1984 | United Kingdom . |
| 2128756 | 5/1984 | United Kingdom . |

Primary Examiner—Joseph A. Orsino
Assistant Examiner—Brent A. Swarthout
Attorney, Agent, or Firm—Stephen L. Borst

[57] ABSTRACT

A gradiomanometer 1 measures the difference in pressure between points 3 and 4 to indicate density and hence proportions of two phases (e.g. liquid and gas), each of known density flowing as indicated by arrow 6. A venturi meter 2 measures the difference in pressure between points 4 and 5 to indicate flow rate, initially assumed to be that of the heavier phase only. An iterative calculation makes it possible to obtain a density measurement corrected to allow for flow friction and individual flow rates of the two components, having regard to slippage therebetween. A step discontinuity 8 may be provided downstream to create turbulence and render the flow homogenous.

5 Claims, 3 Drawing Sheets

MEASURING FLOW IN A PIPE

The present application is related to copending application Ser. No. 017,463.

The present invention provides a method and apparatus for measuring flow in a pipe such as a bore hole, especially two-phase flow.

A venturi meter is one of a number of known devices for measuring the flow rate of one or more liquid or gas phases along a pipe. A differential pressure measurement between two sections of a pipe of different diameters and joined by a smooth change in diameter can be interpreted, using Bernoulli's equation, to provide a measure of momentum change and thus velocity. Venturi meters are useful in pipes such as bore holes because they are more robust and less prone to erosion than other known devices such as the turbine meter. Moreover, they do not intrude into the pipe itself.

In order to calculate the flow rate from the differential pressure measurement of the venturi meter it is necessary to know the density of the fluid. The density of a flowing fluid can be inferred from measurement of a differential pressure along a parallel section of pipe; devices for carrying out such measurements are known as gradiomanometers.

The broad object of the present invention is to provide a particularly simple and robust flow meter incorporating a gradiomanometer and which does not obstruct the pipe.

According to a first aspect of this invention there is provided a flow meter comprising a gradiomanometer and a venturi meter in series in a pipe. From these can be obtained a differential pressure measurement along a parallel section of pipe and a differential pressure measurement between two sections of pipe of different cross-sectional area, with a smooth transition therebetween, i.e. a venturi. The measurement of fluid density by use of the first differential pressure measurement allows a calculation of the flow through the venturi from the second differential pressure measurement.

When fluid flows in apipe there is a contribution to pressure drop along the pipe due to friction between the pipe walls and the fluid contacting the walls. This friction loss is proportional to the square of the flow velocity and inversely proportional to the pipe diameter. In order to obtain a reliable value of density from measurement of diffential pressure using a gradiomanometer it is necessary to take account of, and correct for, the frictional pressure drop.

In single phase flows the density is known or can be measured accurately and the venturi meter can give results with good accuracy. However, in multiphase flows, such as liquid/liquid or gas/liquid (e.g. water/oil or gas/oil) it is impossible to determine from the differential pressure measurement whether there is any difference in velocity, or slippage, between the component phases. Slippage is a source of error in the flow rate calculation since the amount of slippage is influenced by the proportion of each phase, known in the oil industry as the holdup, which in turn influences the overall density of the fluid. In the case of gas/liquid flow, the gas holdup is also referred to as the void fraction.

Neither the slippage nor the friction loss can be calculated explicitly from information available from differential pressure measurements. However, estimates for correction can be obtained.

In a second aspect of the invention there is provided a method of measuring the flow of each phase of a two-phase fluid using a flow meter of the type described above, comprising the steps of calculating flow density on the basis of the first differential pressure measured in the gradiomanometer, calculating flow rate on the basis of the second differential pressure measured in the venturi, applying estimated corrections for slippage and friction loss to the calculated values and reiterating the calculations to obtain an improved flow rate value. This method is based on a appreciation that the density measurement is affected by the initially unknown frictional pressure drop while the flow rate measurement is affected by the initially erroneous density measurement. An itertive procedure makes it possible to approach correct values. We have found that the calculations are rapidly convergent and very few reiterations are necessary, say 2 or 3.

The above described method may be used for the interpretation of measurements in two phase gas/liquid or liquid/liquid flows if the density of the two separate phases is known.

The differential pressure measurements will be misleading if the two-phase fluid is not reasonably homogeneous. The invention further provides a simple and robust flow meter with an integral homogenizer, comprising a pipe formed with, in series, an abrupt change in cross-section for creating turbulence to promote homogenization, a pipe length within which the turbulence may settle, a gradiomanometer and a venturi meter.

Figure 1:
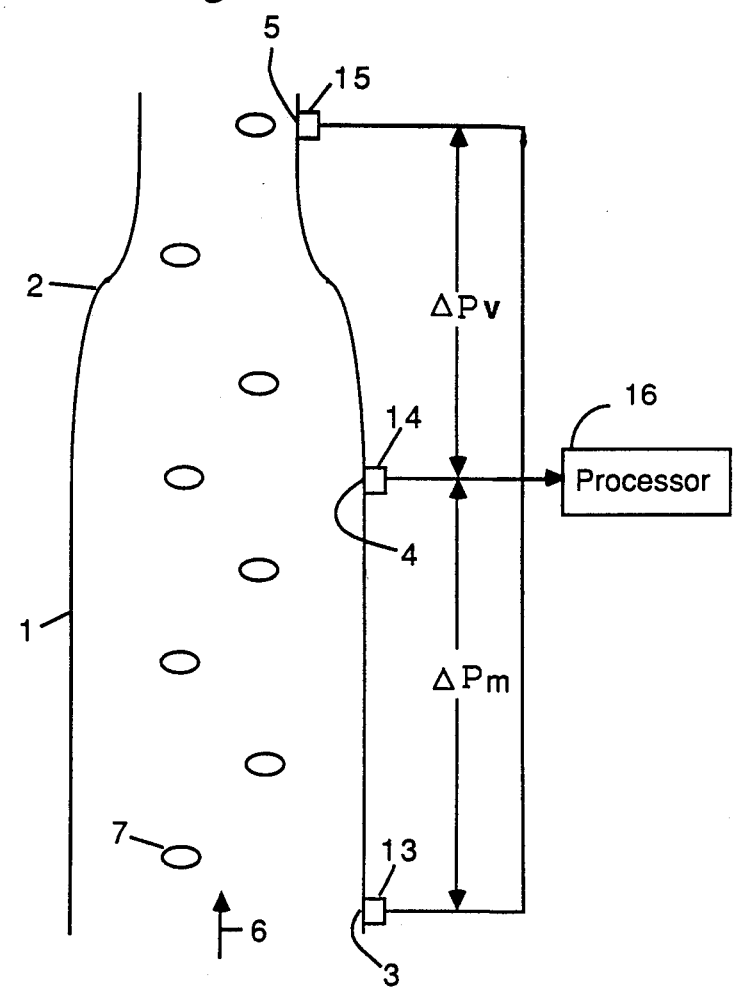
FIG. 1 shows a first embodiment of the invention comprising a gradiomanometer and a venturi meter in series.

FIG. 1 shows a length of pipe with a first section 1 of uniform diameter followed by a section 2 which necks down smoothly to a smaller diameter, forming a venturi. Three pressure transducers, such as are readily commercially available are disposed at points 3, 4 and 5 and are designated as 13, 14, and 15 respectively in the figures. In the event the pressure sensors 13, 14, and 15 are spaced from the pipe but are connected to orifices in the pipe by pressure conducting fluid capillaries (as would be the standard arrangement), the density of the fluid (ordinarily silicon oil) in the capillaries shall be designated as $\rho t$. Instead of three transducers, two differential transducers may be employed, this being the preferred arrangement. The point 4 is at the entrance of the venturi, the point 3 well upstream of the point 4, flow being assumed to be in the direction of the arrow 6, and the point 5 is downstream of the venturi. Thus it is possible to determine the differential pressure $\Delta P_m$ across the gradiomanometer formed by the section 1 and the differential pressure $\Delta P_v$ across the venturi. Bubbles 7 symbolize the light phase in two-phase flow.

To a first approximation, $\Delta P_m$ will enable the mean density and hence the ratio of the two phases (each of known density) to be determined and $\Delta P_v$ will enable the flow rate to be determined on the assumption that the fluid flows as a single phase fluid with the density determined from $\Delta P_m$. However, more accurate results are obtained by means of the following iterative procedure:

For two phase gas/liquid flow where the gas density is much less than the liquid density, it is first assumed that only the liquid phase contributes to the pressure drop through the venturi so that the system can be expressed mathematically by equations 1, 2, and 3 below. (The significance of the notations is described in the Table of Notation below.)

From the venturi pressure drop $\Delta p_v$ a first estimate of liquid velocity $V_{gs}$ may be determined:

$$v_{ls} = K \sqrt{\Delta p_v} \quad (1)$$

where:

$$K = \sqrt{\frac{2}{\rho_l[(d_4/d_5)^4 - 1]}} \quad (2)$$

$$v_{gs} = 0 \quad (3)$$

Then from the gradiomaometer pressure drop $\Delta \rho_m$ a first estimate of gas holdup $y_g$ is obtained:

$$y_g = \frac{\Delta p_m + (\rho_l - \rho_l)gh_m + F_m}{(\rho_l - \rho_g)gh_m} \quad (4)$$

where:

$$F_m = \frac{2f\rho_m h_m (v_{ls} + v_{gs})^2}{d} \quad (5)$$

Here $f$ is a friction factor for the pipe (dependent on the Reynolds number of the flow) and $\rho_m = y_g \rho_g + y_l \rho_l$. At this point if $y_g = 0$ then there is only one liquid flowing and the flow rate is given by the first estimates of $v_{ls}$ of equation 1. If however there is a positive value of $y_g$ then a second estimate of gas velocity is obtained from the slip relationships:

$$v_g = v_b y_l^k + c_o(v_{ls} + v_{gs}) \quad (6)$$

where:

$$v_b = C \left( \frac{\sigma g (\rho_l - \rho_g)}{\rho_l^2} \right)^{\frac{1}{4}} \quad (7)$$

Then:

$$v_{gs} = v_g y_g \quad (8)$$

Using the first estimate for gas velocity (equation 6) and the first estimate of gas holdup (equation 4) the venturi pressure drop can be reinterpreted to give a second estimate of liquid velocity:

$$v_{ls} = K_{yl} \sqrt{\Delta p_v + (\rho_l - \rho_m)gh_v} \quad (9)$$

At this point, the first iteration is complete and the procedure can be checked for convergence. If the current estimates of velocities and holdup are within a certain specified tolerance, then the iteration is finished and we have the final values of $v_{l3}$, $v_{gs}$ and $y_g$. If convergence has not been reached then the procedure is repeated from equation 4 using in equations 5 and 6 a new value of $\rho_m$ (determined from the first estimate of $y_g$ and the equation $\rho_m = Y_g \rho_g + Y_l \rho_l$) and the first estimates of $v_{ls}$ and $v_{gs}$.

In the case of liquid/liquid flows the detail of the equations would change, but the basic interpretation scheme would be similar.

The foregoing equations assume that the flow meter is vertical. To allow for the possibility of inclination, the quantities $h_v$ and $h_m$ appearing in the equations must be multiplied by $\cos \theta$ where $\theta$ is the angle of inclination.

In two phase flow through a venturi the measured pressure drop needs to be corrected for the hydrostatic contribution from the mixture density. The higher the degree of homogeneity of the flow (i.e. the lower the void fraction or light phase holdup) the more nearly will the measured pressure drop correspond to the theoretical true pressure drop, with consequent improvement in the accuracy and/or reliability of calculated flow rate. It is particularly preferred if the homogenizer is a non-obstructive homogenizer since this will allow full bore flow in the pipe. In the embodiment shown schematically by way of example in FIG. 2 a flow meter comprising a gradiomanometer 1 and a venturi 2 of the type previously described is provided in a pipe length downstream of a pipe section 8 which has a step change in diameter from a small diameter d to a larger diameter D. Turbulent stresses caused by the sudden expansion of cross sectional area of the flow cause homogenization of the flow by turbulent mixing.

Figure 2:
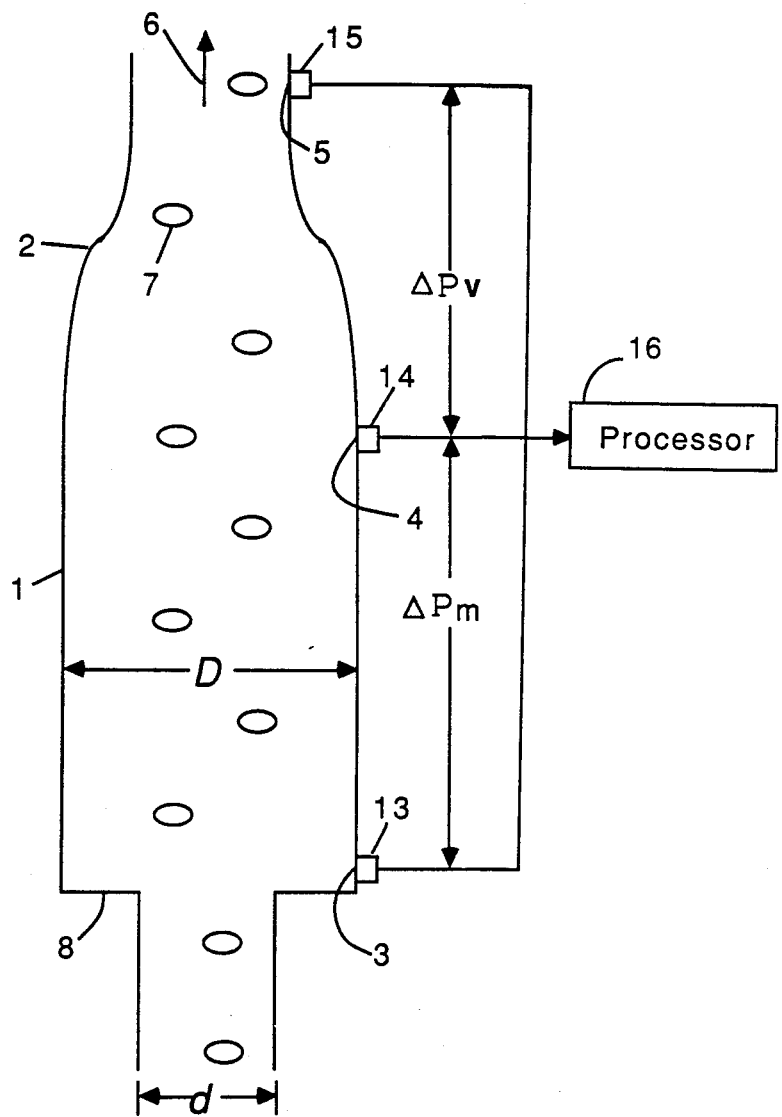
FIG. 2 shows an alternative embodiment with an integral homogenizer.

The flow meters shown in FIGS. 1 and 2 are suitable for use in a borehole, the small diameter d being matched to the size of the casing in the borehole. The larger diameter D may be only 10% greater than the smaller diameter d and be capable of accommodation within the borehole. In an alternative, shown schematically in FIG. 3, the venturi is shown changing from a large diameter to a minimum then back to the large diameter, which corresponds to the diameter of the casing in the borehole. There is no portion of the meter with a diameter exceeding the casing diameter.

Figure 3:
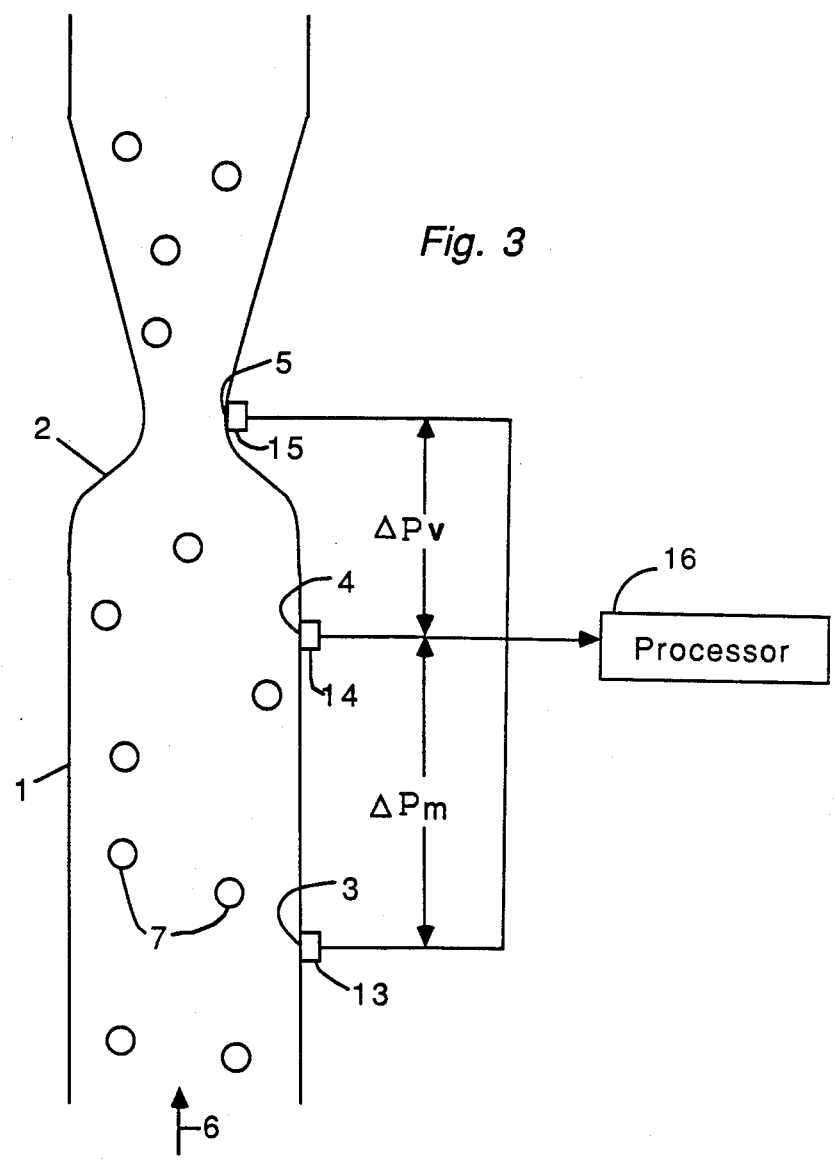
FIG. 3 shows a modified form of the first embodiment.

Although there is some constriction of the pipe cross-section in the embodiment of FIG. 3, in all embodiments there is an unimpeded channel right through the flowmeter. If this is installed down a borehole it remains possible to drop tools through the flowmeter to perform logging and other operations at lower levels.

In all embodiments the gradiomanometer is show immediately upstream of the venturi where the pipe diameter is a maximum because this means that the errors caused by frictional pressure drop are minimized. This does not preclude any other position, although it is desirable to have the gradiomanometer as close to the venturi throat as is possible. A complete system for obtaining real time values for $v_{ls}$, $v_{gs}$ and $y_g$ can comprise the device shown in FIG. 1, 2 or 3 with the transducers 13, 14 and 15 providing data to a computer programmed to implement the equations (1) to (9). In the case of a flowmeter down a borehole, conventional telemetry techniques can be used to convey raw data to a computer at the surface or so to convey results data to the surface from a computer down the bore hole.

| NOTATION | |
|---|---|
| Symbols | |
| C | constant in bubble slip relationship |
| $c_o$ | constant in bubble slip relationship |
| d | diameter |
| h | distance between transducer points 3,4,5 |

| | -continued |
|---|---|
| | NOTATION |
| f | friction factor (non-dimensional) |
| F | friction correction term (units of pressure) |
| g | acceleration due to gravity |
| k | constant in bubble slip relationship |
| K | constant in venturi equation |
| $N_{Re}$ | Reynolds Number |
| p | pressure |
| v | velocity |
| y | holdup (sum of all holdups is equal to 1) |
| $\Delta$ | difference |
| $\rho$ | density |
| $\sigma$ | surface tension |
| | Subscripts |
| 3 | point 3 in gradiomanometer |
| 4 | point 4 in gradiomanometer |
| 5 | point 5 in venturi |
| b | bubble in standing liquid |
| g | gas phase |
| l | liquid phase |
| m | gradiomanometer |
| s | superficial (averaged over entire pipe area) |
| t | fluid in the lines to the pressure transducer |
| v | venturi |

We claim:

1. A full bore, multi-hase fluid flowmeter having no internal obstructions comprising;
   a first section of pipe with a first diameter;
   a second section of pipe with a second diameter less than said first diameter;
   a third section of pipe intermediate and connecting said first and second pipe sections and having a smoothly and gradually changing diameter from said first diameter to said second diameter;
   a first pressure sensor positioned in the neighborhood of the start of the change of diameter of said third section of pipe from said first diameter to said second diameter;
   a second pressure sensor in said first section of pipe spaced in one direction from said first pressure sensor;
   a third pressure sensor spaced in the other direction from said first pressure sensor;
   whereby, the density of the fluid flowing through the pipe obtained from a first differential pressure measurement made between said first and second pressure sensors is combined with the flow rate of the fluid flowing through the pipe sections obtained from said density value and a second differential pressure measurement made between said first and third pressure sensors to obtain a multi-phase fluid flow determination compensated for phase slippage and friction pressure losses.

2. A flow meter according to claim 1, further comprising a non-obstructive homogenizer connected to the end of said first section of pipe not connected to said third section of pipe, said non-obstructive homogenizer consisting of a pipe section which has an abrupt change in cross-section for creating turbulence.

3. A method of measuring the flow rate of a two-phase fluid comprising a lighter and a heavier phase, using a gradiomanometer and a venturi meter in series in a pipe, comprising the steps of:

a. measuring a first differential pressure in the gradiomanometer;
   b. measuring a second differential pressure in the venturi;
   c. calculating an estimated vaue of the mean flow density on the basis of the first differential pressure measurement;
   d. calculating an estimated value of the flow rate of said heavier phase on the basis of the second differential pressure;
   e. correcting the estimated value of the mean flow density for friction loss between the fluid and the gradiomanometer from the second differential pressure measured in the venturi; and
   f. correcting the estimated value of the heavier phase flow rate for the velocity differences between the component phases of the two phase fluid from the first differential pressure measured in the gradiomanometer.

4. A method according to claim 3, wherein the correcting steps comprise:
   a. calculating the proportion of at least one phase in said two-phase fluid from the estimated value of the mean flow density;
   b. calculating the flow rate of said one phase from a predetermined liquid phase velocity difference relationship;
   c. calculating the frictional component of the pressure drop in the gradiomanometer using the flow rate calculated in step b;
   calculating a corrected value of the mean flow density and said proportion of said at least one phase from the first differential pressure and from the frictional component of the pressure drop in the gradiomanometer; and
   e. re-iterating the above steps un til convergence is reached.

5. A method of measuring the flow rate of a two-phase fluid wherein the fluid is passed through a gradiomanometer providing a first measurement representative of fluid density, and through a venturi flow meter providing a second measurement representative of flow rate and the following calculations are re-iterated to improve the accuracy of the measurements:
   a. calculate the frictional pressure drop along the gradiomanometer on the basis of the flow rate provided by the second measurement;
   b. calculate the proportion of the lighter phase on the basis of the density provided by the first measurement corrected by the frictional pressure drop;
   c. calculate the flow rate of the lighter phase in accordance with the calculated proportion of the lighter phase and a predetermined liquid phase velocity difference relationship;
   d. re-calculate the flow rate of the heavier phase from the second measurement and in accordance with the proportions of the two phases and the calculated flow rate of the lighter phase;
   e. re-iterate steps a to d but with the flow rate utilized in step a replaced by the flow rate re-calculated in step d.

* * * * *